United States Patent [19]
Lemoine et al.

[11] Patent Number: 6,054,443
[45] Date of Patent: Apr. 25, 2000

[54] **EXOCELLULAR POLYSACCHARIDE PRODUCED BY *STREPTOCOCCUS THERMOPHILUS***

[75] Inventors: Jérôme Lemoine, Lille, France; Jean-Richard Neeser, Savigny, Switzerland

[73] Assignee: Nestec S.A., Vevey, Switzerland

[21] Appl. No.: 09/094,301

[22] Filed: Jun. 9, 1998

[30] Foreign Application Priority Data

Jul. 5, 1997 [EP] European Pat. Off. ............... 97111381

[51] Int. Cl.⁷ .......................... A61K 31/715; C07H 1/08; C08B 37/00
[52] U.S. Cl. .......................... 514/54; 536/123; 536/123.1; 536/127
[58] Field of Search ........................ 514/54, 61; 536/123, 536/123.1, 127

[56] References Cited

U.S. PATENT DOCUMENTS 3,985,901  10/1976  Gonzalez Barberan .................. 426/43

FOREIGN PATENT DOCUMENTS

| 0 063 438 | 4/1981 | European Pat. Off. . |
| 0 298 605 | 1/1989 | European Pat. Off. . |
| 0 331 564 | 9/1989 | European Pat. Off. . |
| 0 699 689 | 3/1996 | European Pat. Off. . |

OTHER PUBLICATIONS

Thorkild's Lectin Page (http://plab.ku.dk/tcbh/lectin-links.htm), Sep. 1996.

Elgavish et al., "Lectin–carbohydrate interactions: different folds, common recognition principles", TiBS, vol. 22: 462–467, Dec. 1997.

Lemoine et al. "Structural Characterization of the Exocellular Polysaccharides Produced by *Streptococcus thermophilus* SFi39 and SFi12", Applied and Environmental Microbiology, vol. 63(9): 3512–3518, Sep. 1997.

Stingele et al., "Identification and Characterization of the eps (Exopolysaccharide) Gene Cluster from *Streptococcus thermophilus* Sfi6", Journal of Bacteriology, vol. 178(6): 1680–1690, Mar. 1996.

Stingele et al. "Disruption of the gene encoding penicillin–binding protein 2b (pbp2b) causes altered cell morphology and cease in exopolysaccharide production in *Streptococcus thermophilus* Sfi6", Molecular Microbiology, vol. 22(2): 357–366, 1996.

J. Cerning et al. "Exocellular polysaccharide production by *Streptococcus thermopilus*", Biotechnology Letters, vol. 10, No. 4, 1988, pp. 255–260.

Barondes et al., "Galectins: A Family of Animal β–Galactoside–Binding Lectins", Cell, vol. 76, 597–598, 1994.

Hughes et al., "Mac–2: a versatile galactose–binding protein of mammalian tissues" Glycobiology 4, No. 1, 5–12, Feb. 1994.

Truong et al., "Human Neurtophils Express Immunoglobulin E (IgE)–Binding Proteins (Mac–2/εBP) of the S–Type Lectin Family: Role in IgE–dependent Activation"; Journal of Experimental Medicine, vol. 177, 243–248, 1993.

Wollenberg et al., "Human Keratinocytes Release the endogenous β–Galactoside–binding Soluble Lectin Immunoglobulin E (IgE–Binding Protein) which binds to Langerhans Cells Where It Modulates Their Binding Capacity for IgE Glycoforms"; Journal of Experimental Medicine, vol. 178, 777–785, 1993.

Kolenbrander et al., "Coaggregation: specific adherence among human oral plaque bacteria"; The FASEB Journal, vol. 7, 406–412, 1993.

Dubois et al.; "Colorimetric Method for Determination of Sugars and Related Substances", Analytical Biochemical., 28, No. 3, 350–356, Mar. 1956.

Neeser et al.; "A Quantitative Determination by Capillary Gas–Liquid Chromatography of Neutral and amino Sugars (as O–Methyloxime Acetates), and a Study on Hydrolytic Conditions for Glycoproteins and Polysaccharides in Order to Increase Sugar Recoveries"; Analytical BioChemistry, vol. 142, 58–57 (1984).

*Primary Examiner*—Howard C. Lee
*Attorney, Agent, or Firm*—Pennie & Edmonds LLP

[57] ABSTRACT

The invention relates to a new isolated polysaccharide originating from *Streptococcus thermophilus* comprising the following repeat structure, and which may be use for the preparation of a food, cosmetic or pharmaceutical composition intended for inhibiting β-galactoside specific lectins.

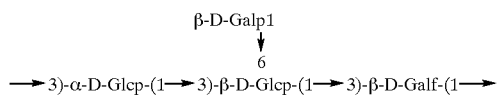

3 Claims, No Drawings

EXOCELLULAR POLYSACCHARIDE PRODUCED BY *STREPTOCOCCUS THERMOPHILUS*

TECHNICAL FIELD

The present invention relates to a new exocellular polysaccharide (EPS) originating from *Streptococcus thermophilus*.

STATE OF THE ART

The biological communication (the possibility for a cell to recognize a molecule or another cell) is a central phenomenon in pathological as well as in the normal state. Among the various mechanisms of molecular recognition between cells, and/or between cells and molecules, the binding of specific glycosidic structures by specialized proteins, called lectin, is today considered as a major molecular recognition system.

Dealing with a class of mammalian lectins recognizing galactose residues, membership in the galectin family requires fulfillment of two criteria: affinity for β-galactosides and significant sequence similarity in the carbohydrate-binding site, the relevant amino acid residues which have been determined (Barondes et al., Cell, 76, 598, 1994). Since galectins may be bound specifically and non-covalently to well-defined glycosidic sequences, P-gal-containing polysaccharides may thus be used in-vitro or in-vivo to inhibit specifically the binding of galectins and their receptors, an effect which may modulate many biological systems including pathological situations (EP699689; Hughes et al., Glycobiology, 4, 5–12, 1994; Truong et al., Journal of Experimental Medicine, 177, 243–248, 1993; Wollenberg et al., Journal of Experimental Medicine, 178, 777–785, 1993).

Such polysaccharides may also be used for inhibiting microbial β-galactoside specific lectins, for example those modulating coaggregations of human oral plaque bacteria. Indeed, proteinaceous surface molecules (called adhesins) on one plaque cell type recognize carbohydrate receptors on partner plaque bacteria in most of the coaggregations studied so far. Many of those coaggregations are known to be inhibitable by lactose or other β-galactoside derivatives (Kolenbrander et al., The FASEB Journal, 7, 406–412, 1993).

Finally, there have been many prior studies upon polysaccharides produced by microorganisms and, in recent years, there have been several reports of studies on the structure of exocellular polysaccharides obtained by lactic acid bacteria and on their biological activities. For instance, a polysaccharide consisting of galactose, glucose and N-acetylgalactosamine (2:1:1) may be obtained from the strains *Streptococcus thermophilus* CNCM I-733, CNCM I-734 and CNCM I-735 (see EP 331564). In addition, EP750043 discloses the genes and proteins from *Streptococcus thermophilus* CNCM I-1590 involved in the biosynthesis of this type of exopolysaccharide.

SUMMARY OF THE INVENTION

The aim of the present invention is to provide a new polysaccharide which can be used to inhibit the binding of β-galactoside specific lectins and their receptors. This aim is achieved by the isolation of a polysaccharide originating from *Streptococcus thermophilus*. This polysaccharide can be used to prepare a composition which inhibits β-galactoside specific lectins including microbial lectins. These compositions can be in the form of a food, a cosmetic composition or a pharmaceutical composition, and include an effective amount of the polysaccharide.

DETAILED DESCRIPTION OF THE INVENTION

In the following description the term "β-galactoside specific lectin" designates all carbohydrate-binding proteins specific for β-galactosides, from plant, mammalian, microbial and virus sources. Any β-galactoside specific toxin produced by microbes should also be considered as a lectin in the context of the present invention.

The present invention concerns a new isolated exopolysaccharide ("EPS") originating from *Streptococcus thermophilus* comprising the following repeat structure:

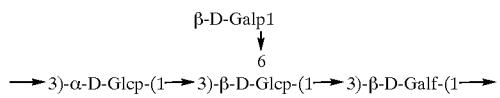

According to a preferred embodiment, the EPS of the invention which originates from *Streptococcus thermophilus* only possesses the above repeat structure.

An EPS according to the present invention may be naturally produced by *Streptococcus thermophilus* strains, in particular by the strain CNCM I-1879 which has been deposited under the Budapest Treaty in Jun. 20, 1997, at the Collection Nationale de Culture de Microorganismes (CNCM), 25 rue du docteur Roux, 75724 Paris, France.

Details on this strain with respect to its morphology and sugar fermentation pattern are as follows.

Morphology: isolated diplococcies or in form of short chains.

Sugar fermentation: glucose, lactose and sucrose.

The invention also has for object the use of this EPS for the preparation of a composition intended for inhibiting β-galactoside specific lectins, especially for inhibiting β-galactoside microbial lectins, i.e. for inhibiting coaggregations of human oral plaque bacteria. According to a preferred embodiment such composition, comprising an effective amount of this EPS for inhibiting β-galactoside specific lectins, may be administered orally to a human in need thereof.

The present invention also has for object a food, a cosmetic or a pharmaceutical composition comprising as additive an effective amount of this EPS for inhibiting β-galactoside specific lectins, especially for inhibiting β-galactoside microbial lectins, i.e. for inhibiting coaggregations of human oral plaque bacteria. Such composition may be prepared by isolating the EPS followed by the addition of the isolated EPS to a food, a cosmetic or a pharmaceutical composition adapted for the purpose and method of consumption or application.

Isolation of the EPS according to the invention may require the removal of proteins and bacteria from a lactic fermented culture, for example of the strain CNCM I-1879, and then isolation of the EPS. Removal of proteins and bacteria may be achieved by precipitation with a solution of alcohol or trichloroacetic acid followed by centrifugation, whereas isolation of EPS may be achieved by precipitation with another solvent (acetone) followed by centrifugation, for example. If necessary, the EPS may be further purified by gel-filtration or with an affinity column, for example.

In the context of the present invention, isolation of the EPS according to the invention also encompasses any method of EPS production by fermentation followed by a concentration of the constituents in the medium. Concentration may thus be achieved by any method known to the skilled person, in particular by lyophilisation or spray-drying methods, for example (see U.S. Pat. No. 3,985,901, EP298605 or EP63438).

Finally, the present invention also has for object a food, a cosmetic or a pharmaceutical composition comprising a killed bacteria having produced in-situ the EPS according to the invention, or a living bacteria producing or having produced in-situ the EPS according to the invention.

The present invention is not to be limited in scope by the specific embodiments described herein. Indeed, various modifications of the invention, in addition to those described herein, will become apparent to those skilled in the art from the foregoing description. Such modifications are intended to fall within the scope of the claims. Various publications are cited herein, the disclosures of which are incorporated by reference in their entireties to the extent necessary for understanding the present invention. In the following description, the percentages are given by weight except where otherwise stated. The following examples are preceded by a description of the EPS characterization and purification according to the invention.

Bacterial Strain and Fermentation Conditions: *Streptococcus thermophilus* CNCM I-1879 is a ropy strain from the Nestle strain collection. The growth medium was skimmed milk powder reconstituted at 10% and heat-treated (115° C., 35 min) for sterilization (9 parts), plus an amino acid mixture (1 part; 495 mg/l Ala, 343 mg/l Arg, 682 mg/l Asp, 59 mg/l Cys, 1229 mg/l Glu, 759 mg/l Gly, 153 mg/l His, 215 mg/l Iso, 470 mg/l Leu, 565 mg/l Lys, 122 mg/l Met, 255 mg/l Phe, 436 mg/l Pro, 68 mg/l Ser, 170 mg/l Thr, 61 mg/l Try, 304 mg/l Val) adjusted to pH 5.0 with 1M NaOH and filtered for sterilization. The fermentation was carried out in a 1 liter-scale fermentor for 24 h at 40° C. with an inoculum of 1%. The pH was maintained at 5.5 by using 2N NaOH and a stirring rate of 60 RPM.

Extraction of the Polysaccharide: the removal of proteins and bacteria from the spent fermented cultures was achieved by the addition of an equal volume of a solution of trichloroacetic acid (TCA, 40%), followed by centrifugation (17,000×g, 20 min). Then, the same volume of acetone was added to the supernatant fraction to precipitate the EPS, which was finally collected by centrifugation (17,000×g, 20 min). Such precipitated EPS fractions were dissolved in distilled water and the pH was adjusted to 7.0 with a sodium hydroxide solution. After dialysis against distilled water (16 h), insoluble material was removed by ultracentrifugation (110,000×g, 1 h) and the EPS was lyophilized. Total neutral sugar content of this crude dehydrated EPS was determined by the phenol-sulphuric acid method (Dubois et al., Anal. Chem., 28, 350–356, 1956). This extraction yielded 350 mg of EPS.

Size of the Exopolysaccharide: gel-filtration chromatography was conducted to confirm the purity and to estimate the molecular weight of the polysaccharide using a FPLC system (Pharmacia) with a Superose 6 column (10 cm×30 cm). Samples (200 μl) containing 200–400 μg dehydrated polysaccharide were applied onto the column, and eluted with 50 mM phosphate buffer at pH 7.2 at the rate of 0.5 ml/min. Fractions of 1.0 ml were collected and the total neutral sugar content in each fraction was determined by the phenol-sulphuric acid method. EPS was eluted at the exclusion limit (approximately 2×10$^6$ Da).

Monosaccharide Composition: monosaccharide composition was first determined by gas-liquid chromatography (GLC) of O-methyloxime acetate derivatives obtained after acid hydrolysis of the polysaccharide (1 h, 125° C.) in a 4 N trifluoroacetic acid (TFA) solution (Neeser et al., Anal. Biochem., 142, 58–67, 1984). Independently, polysaccharide samples (0.1 mg) were methanolyzed (methanolic 0.5N HCl, 80° C., 24 h), and the trimethylsilylated N-reacetylated methyl glycosides were analyzed using a Varian 3400 gas chromatograph (temperature program: 120° C. to 240° C. at 2° C./min) on a BP1 fused-silica capillary column (25 mm×0.32 mm, SGE). The absolute configuration of the monosaccharides was also determined by GLC, using the trimethylsilylated N-reacetylated (−)-2-butyl glycoside derivatives. Results show the presence of D-galactose and D-glucose in a molar ratio of 1:1.

Nuclear Magnetic Resonance Spectroscopy: the 400 MHz $^1$H-NMR experiments were performed with a Bruker AM-400 wide bore spectrometer equipped with a 5 mm $^1$H/$^{13}$C dual probe head, operating in the pulsed Fourier transform mode and controlled by an Aspect 3000 computer. All spectra were obtained at a probe temperature of 333° K. For one-dimensional spectra, a 90-degree pulse of 10.6 μs and 1 s recycle delay were used. The chemical shifts are given relative to the signal of the methyl group of acetone (δ 2.225 for $^1$H and 31.55 for $^{13}$C).

The 2D-homonuclear COSY 45, COSY with simple, double, and triple relay transfers were performed by means of the standard Bruker pulse program library, or the programs given by B. Perly (CEA Saclay, France). For all Relayed Coherence Transfer (RTC) experiments, refocusing delays of 35 ms were chosen and the relaxation delay was 2s. In all these experiments, the spectral width was 1840 Hz, the $^1$H 90-degree pulse was 10.6 μs; 256W×2K FID data matrices were acquired, which were zero-filled prior to Fourier transform, to obtain a 1K×2K spectral data matrix; a sine-bell squared filter function was used in both dimensions.

The 2D-$^{13}$C/$^1$H COSY experiments were performed with simultaneous suppression of $^1$H homonuclear couplings by means of the standard Bruker pulse program XHCORRD. Refocusing delays were adjusted to an average $^1J_{C,H}$ coupling constant of 150 Hz. $^1$H and $^{13}$C 90-degree pulse width were 10.6 and 6 μs, respectively. The relaxation delay was 0.8s. A 128W×4K FID data matrix was acquired, which was zero-filled prior to Fourier transform, to obtain a 512W×4K spectral data matrix. An exponential function (LB=1 Hz) for $^3$C-subspectra and a sine-bell filter function for $^1$H-spectra were applied to enhance the signal to noise ratio.

For clarity in the presentation of the NMR data, the numbering of the sugar residues (capital letters) and protons of each residue (arabic numerals) deduced from the assignment procedure will be used here in advance:

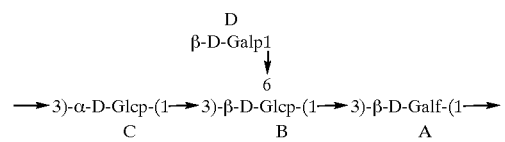

The $^1$H-NMR spectrum of the native CNCM I-1879 EPS shows the presence of four anomeric protons. The set of vicinal coupling constants depicted on the $^1$H-COSY spectrum allowed the identification of the monosaccharides as α-Glc (C), β-Glc (B), and β-Gal (D), respectively. According to the results of the sugar composition analysis (Gal/Glc 1:1), and to the characterization from the native polysaccharide of a 1,3,4 tri-O-methyl hexose among the methyl ether derivatives (see methylation analysis below) we concluded that A residue was a galactofuranose. Its $^3J_{1,2}$ which is lower than 2 Hz is characteristic of the β anomeric conformation. Finally the two step-relayed COSY spectra allowed the complete assignment of the proton resonances (table 1). Then, via the $^1H-^{13}C$ heteronuclear correlation spectrum, the 24 $^{13}C$ atom resonances were fully assigned. These values clearly show the deshielding of C-3 for α-Glcp (C), C-3 for β-Galƒ (A), C-6 for β-Glc (B), whereas the $^{13}C$ resonances of β-Gal (D) were specific of a non-reducing monosaccharide unit.

TABLE 1

$^1H$ chemical shifts for the native polysaccharide from CNCM I-1879

| | Chemical shift (δ) in residue | | | |
|---|---|---|---|---|
| Proton | C →3-α-D-Glcp | B →3(6)-β-D-Glcp | A →3-β-D-Galƒ | D β-D-Galp |
| H-1 | 5.373 | 4.7 | 5.358 | 4.886 |
| H-2 | 3.741 | 3.491 | 4.414 | 3.628 |
| H-3 | 3.911 | 3.725 | 4.359 | 3.695 |
| H-4 | 3.548 | 3.777 | 4.31 | 3.989 |
| H-5 | 4.07 | 3.702 | 4.014 | 3.729 |
| H-6 | 3.88 | 4.234 | 3.77 | 3.85 |
| H-6' | 3.818 | 3.936 | 3.714 | 3.82 |

TABLE 2

$^{13}C$ chemical shifts for the native polysaccharide from CNCM I-1879

| | Chemical shift (δ) in residue | | | |
|---|---|---|---|---|
| Proton | C →3-α-D-Glcp | B →3(6)-β-D-Glcp | A →3-β-D-Galƒ | D β-D-Galp |
| C-1 | 100.00 | 102.99 | 109.37 | 104.42 |
| C-2 | 72.50 | 72.72 | 80.70 | 71.84 |
| C-3 | 81.09 | 83.61 | 85.39 | 73.81 |
| C-4 | 69.07 | 70.82 | 83.20 | 69.70 |
| C-5 | 72.84 | 73.70 | 71.40 | 76.03 |
| C-6 | 61.62 | 69.54 | 63.97 | 61.94 |

Methylation analysis: for achieving the complete elucidation of the repeating unit sequence, methylation analysis of the native polysaccharide and of three oligosaccharides derived from it was performed. Among these 3 oligosaccharides obtained by acid hydrolysis, one was obtained from the periodate-oxidized derivative of the EPS, whereas two were derived from the native EPS. The obtention of the three oligosaccharides and the methylation analysis were achieved as follows.

Periodate-oxidation of the EPS: 10 mg-samples of polysaccharide were dissolved in 10 ml of sodium acetate buffer, pH 3.9. Sodium metaperiodate was added to a final concentration of 0.05M, and the solution was maintained in the dark for 7 days at 4° C. Then, the excess of periodate was reacted with 2 ml of ethylene glycol for 2 h at room temperature, and the mixture was dialyzed against bidistilled water for 48 h and lyophilized. The oxidized polysaccharide was reduced with NaBH$_4$ (16 h) and the excess of NaBH$_4$ was reacted with a Dowex 50×8 (H$^+$) resin, followed by vacuum co-evaporation with methanol to remove boric acid. The oxidized and reduced polysaccharide was finally subjected to mild acid hydrolysis in 0.5N TFA during 1 h at 90° C. After removal of TFA by vacuum drying, the resulting oligosaccharides were fractionated by HPAE-PAD chromatography (see below).

Partial acid hydrolysis: polysaccharide samples (10 mg) were hydrolyzed in 4 ml of a 0.2N TFA solution, during 1 h at 100° C. The degree of polysaccharide hydrolysis and the obtention of low mass oligosaccharides were followed by thin layer chromatography on Silica Gel 60 F254 aluminium sheets (Merck) developed in a butanol/water/acetic acid (2:1:1:5) mixture, the sugars being detected with an orcinol-sulfuric acid solution. To recover the hydrolyzed polysaccharides, TFA was removed by vacuum evaporation and lyophilization. Direct fractionation of the oligosaccharide mixture was performed by high pressure anion exchange—pulse amperometric detection chromatography (HPAE-PAD: see below).

HPAE-PAD chromatography: a Dionex system was used, consisting of a Dionex Bio-LC quaternary gradient module, a PAD 2 detector, and a Carbopac PA-1 pellicular anion exchange column (250×9 mm). The elution program was as follows: 100% eluant A (0.1N NaOH) for 5 min, then 75 % eluant A—25% eluant B (0.1N NaOH containing 1N CH$_3$COONa) for 60 min, with a flow rate of 3 ml/min. The eluted fractions were immediately neutralized with 1N acetic acid and lyophilized. The fractions were successively desalted on a column (6×1 cm) of Dowex 50×8 (H$^+$) resin, then on a column of Fractogel HW40F (55×2 cm) using water as eluant.

Methylation: polysaccharides or oligosaccharides derived from mild acid hydrolysis were permethylated, subjected either to methanolysis or to strong acid hydrolysis (TFA 4N, 4h, 100° C.) followed by reduction with BD$_4$Na, and finally acetylated (pyridine, acetic anhydride 1:2). The resulting methylglycosides and alditols were identified by GLC-mass spectrometry on the electron impact mode, with a Nermag R10-10S mass spectrometer on the electron energy of 70 eV and an ionizing current of 0.2 mA.

Results are presented in table 3.

TABLE 3

Methylation analysis (methylglycoside and itol-acetate derivatives) of the native EPS, of oligosaccharide I derived from the EPS hydrolyzed after periodate oxidation (itol-acetates derivatives), and of oligosaccharides III and IV derived from partial acid hydrolysis of the native EPS (itol-acetates derivatives).

| | Molar ratio | | | |
|---|---|---|---|---|
| Derivative | EPS | OS/I | OS/III | OS/IV |
| 1,2,4,5 Ara | — | 0.3 | — | — |
| 1,2,4,5,6 Gal | — | — | 0.7 | 1.1 |
| 2,3,4,6 Gal | 1.0 | — | 1.0 | 1.0 |
| 2,3,4,6 Glc | — | 1.0 | — | 0.7 |
| 2,5,6 Galƒ | 1.0 | — | — | — |
| 2,4,6 Glc | 1.3 | 0.9 | — | — |
| 2,3,4 Glc | — | — | 1.6 | — |
| 2,4 Glc | 0.9 | — | — | 1.0 |

By combining the methylation data for oligosaccharides III (Gal1→6Glc1→3Gal-ol) and IV (Glc1→3(Gal1→6) Glc1→3Gal-ol), a repeating unit was deduced, and further confirmed by the trisaccharide I obtained after periodate oxidation and hydrolysis, which led to a linear structure having only 1→3 linkage positions (Gal1→3Glc1→3Gal-ol). Thus, the following repeating unit sequence was elucidated:

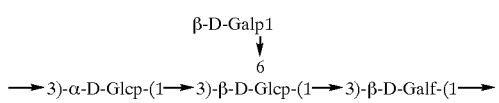

EXAMPLES

The invention is further described by in the following non-limiting examples, which are set forth for illustrating the most preferred embodiments.

Example 1

Set-style acidified milk

Set-style acidified milk comprising the *S. thermophilus* CNCM I-1879 strain was obtained by the following process.

To a whole milk comprising 3.7% fat, 2.5% skimmed milk powder and 1% yeast extract were added. 40 liters of this milk were pasteurized at 92° C. for six minutes, homogenized at 75° C. and 150 bars (two levels) and cooled at a temperature around 42° C. The freeze-dried *S. thermophilus* CNCM I-1879 strain was reactivated with several successive cultures in a sterile MSK medium (skimmed milk powder reconstituted at 10%, comprising 0.1% of a commercial yeast extract). The sterilized milk was inoculated with 1% of the culture of *S. thermophilus* strain taken at the medium coagulation stage. The milk was incubated at 42° C. until reaching a pH around 4.65, and then cooled at a temperature of 4° C.

Example 2

Purification of the EPS

To a whole milk comprising 3.7% fat, 2.5% skimmed milk powder and 1% yeast extract were added. 40 liters of this milk were pasteurized at 92° C. for six minutes, homogenized at 75° C. and 150 bars (two levels) and cooled at a temperature around 42° C. The freeze-dried *S. thermophilus* CNCM I-1879 strain was reactivated with several successive cultures in a sterile MSK medium (skimmed milk powder reconstituted at 10%, comprising 0.1% of a commercial yeast extract). The sterilized milk was inoculated with 1% of the culture of *S. thermophilus* strain taken at the medium coagulation stage. The milk was incubated at 40° C. The pH was maintained at 5.5 by using 2N NaOH and a stirring rate of 60 rpm during 24 hours.

The removal of proteins and bacteria from the fermented culture was achieved by the addition of an equal volume of a solution of trichloroacetic acid (TCA, 40%), followed by centrifugation (17,000×g, 20 min). Then, the same volume of acetone was added to the supernatant fraction to precipitate the EPS, which was finally collected by centrifugation (17,000×g, 20 min). Such precipitated EPS fractions were dissolved in distilled water and the pH was adjusted to 7.0 with a sodium hydroxide solution. After dialysis against distilled water (16 h), insoluble material was removed by ultracentrifugation (110,000×g, 1 h) and the EPS was lyophilized.

Example 3

Acidified whey milk

Whey milk comprising the *S. thermophilus* CNCM I-1879 strain was obtained by the following process.

A sweet lactoserum powder was reconstituted at 12.5% in water, 1% yeast extract was added, 40 liters of this whey were pasteurized at 92° C. for six minutes, homogenized at 75° C. and 150 bars (two levels) and cooled at a temperature around 42° C. The freeze-dried *S. thermophilus* CNCM I-1879 was reactivated with several successive cultures in a sterile MSK medium (skimmed milk powder reconstituted at 10%, comprising 0.1% of a commercial yeast extract). The sterilized milk was inoculated with 1% of the culture of the *S. thermophilus* strain taken at the medium coagulation stage. The whey milk was incubated at 42° C. until reaching a pH around 4.65, and then cooled at a temperature of 4° C. Finally, the fermented culture was spray-dryed according to the method described in EP96201922.0 (Société des Produits Nestlé).

Example 4

Pharmaceutical composition for buccal hygiene

| CHEMICAL NAME | TRADE NAME | % WEIGHT |
| --- | --- | --- |
| PHASE A | | |
| PEG-40 Hydrogenated castor oil | Cremophor RH 40 | 0.1 |
| Flavour | Strawberry E 2226 | 0.04 |
| Flavour | Raspberry | 0.1 |
| PHASE B | | |
| Sodium Cyclamate | Sodium Cyclamate | 0.1 |
| Exopolysaccharide preparation from example 2 | | 0.50–5.00 |
| Demineralized water | | 94.66–99.16 |
| TOTAL | | 100 |

Example 5

Cosmetic composition for skin hygiene

| | % WEIGHT |
| --- | --- |
| OIL PHASE | |
| BRIJ 721 (Steareth 21) | 4 |
| Cetyl alcohol | 0.04 |
| Mineral oil | 0.1 |
| Propyl parahydroxybenzoate | |
| WATER PHASE | |
| CARBOPOL 934 (Carbomer 934) | 0.1 |
| Sodium hydroxide (solution at 10%) | 0.1 |
| Methyl parahydroxybenzoate | 0.18 |
| Exopolysaccharide preparation from example 2 | 0.50–5.00 |
| Demineralized water | 75.60–80.10 |
| TOTAL | 100 |

Example 6

Pharmaceutical composition for gastroenterological usage

A pharmaceutical composition was obtained as a capsule which was made with gelatine and water, and which contained from 5 to 50 mg of the exopolysaccharide according to example 2. Alternatively, powdered tablet formulations can be obtained directly from the acidified cultured milks described above, in examples 1 and 3, by freeze-drying these fermented milks and pressing the resulting powder in a form of tablets.

What is claimed is:
1. An isolated expolysaccharide originating from *Streptococcus thermophilus* comprising the following repeat structure
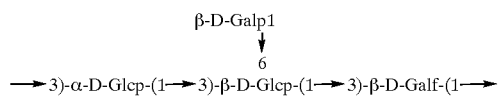
2. A food or cosmetic composition comprising the EPS of claim 1.
3. A food or cosmetic composition comprising the EPS of claim 1 and a strain of bacteria, in live or dead form, capable of producing the EPS of claim 1 in-situ when live.
* * * * *

UNITED STATES PATENT AND TRADEMARK OFFICE
CERTIFICATE OF CORRECTION

PATENT NO.    : 6,054,443

DATED         : April 25, 2000

INVENTOR(S)   : Lemoine et al.

It is certified that error appears in the above-identified patent and that said Letters Patent is hereby corrected as shown below:

Title page , line [30], under Foreign Application Priority Data: please delete "97111881" and insert --97111381.6--.

In Column 9, claim 1, line 1, please change "expolysaccharide" and insert --exopolysaccharide--.

Signed and Sealed this

Twentieth Day of March, 2001

Attest:

NICHOLAS P. GODICI

*Attesting Officer*    *Acting Director of the United States Patent and Trademark Office*